United States Patent [19]

Bindschaedler et al.

[11] Patent Number: 4,968,350
[45] Date of Patent: Nov. 6, 1990

[54] PROCESS FOR PREPARING A POWDER OF WATER-INSOLUBLE POLYMER WHICH CAN BE REDISPERSED IN A LIQUID PHASE, THE RESULTING POWDER AND UTILIZATION THEREOF

[76] Inventors: Christian Bindschaedler, 4 route de Malagny, CH 1294 Genthold; Robert Gurny, 7 rue Calvin, CH 1204 Geneva; Eric Doelker, 24 avenue Dumas, CH 1206 Geneva, all of Switzerland

[21] Appl. No.: 294,516
[22] PCT Filed: Apr. 1, 1988
[86] PCT No.: PCT/EP88/00281
§ 371 Date: Dec. 9, 1988
§ 102(e) Date: Dec. 9, 1988
[87] PCT Pub. No.: WO88/08011
PCT Pub. Date: Oct. 20, 1988

[30] Foreign Application Priority Data
Apr. 16, 1987 [CH] Switzerland .......................... 1497/88

[51] Int. Cl.$^5$ ............................ C08K 3/00; C08L 1/08
[52] U.S. Cl. ..................................... 106/170; 106/198; 523/334

[58] Field of Search ................ 106/170, 198; 523/223, 523/300, 334, 304, 309

[56] References Cited

U.S. PATENT DOCUMENTS

| | | | |
|---|---|---|---|
| 2,809,120 | 10/1957 | Sloan et al. | 106/196 |
| 2,809,192 | 10/1957 | Sloan et al. | 106/196 |
| 3,485,651 | 12/1969 | Ganz | 106/198 |
| 4,462,839 | 7/1984 | McGinley | 106/194 |

FOREIGN PATENT DOCUMENTS 1264953 12/1961 France .
2152936 8/1985 United Kingdom .

Primary Examiner—William R. Dixon, Jr.
Assistant Examiner—Melissa Bonner
Attorney, Agent, or Firm—Stevens, Davis, Miller & Mosher

[57] ABSTRACT

The process for preparing a redispersible powder of a water-insoluble polymer by a producing a gel of a water-soluble macromolecular substance and water. Then a second solution is prepared by mixing a single organic solvent which is partially miscible with water and a water-insoluble polymer. These two solutions are emulsified and then water is added to diffuse the solvent to form microparticles in suspension. The particles are collected by a conventional method.

10 Claims, No Drawings

PROCESS FOR PREPARING A POWDER OF WATER-INSOLUBLE POLYMER WHICH CAN BE REDISPERSED IN A LIQUID PHASE, THE RESULTING POWDER AND UTILIZATION THEREOF

The invention pertains to the area of latexes, dispersions in a liquid phase of water-insoluble polymers, also called pseudo-latexes, and powders of such polymers which can be redispersed in a liquid phase. Specifically, the objective of the invention is a process for preparing a powder of water-insoluble polymer, which can be redispersed in a liquid phase, as well as utilization of such a powder to produce a pseudo-latex.

At present, pseudo-latexes in the liquid dispersion state are manufactured according to the process described in U.S. Pat. No. 4,177,177 and U.S. Pat. No.4,330,338 or according to minor variations thereof. This process consists of dissolving a water-insoluble polymer in an organic solvent which is not miscible with water, emulsifying the resulting solution in an aqueous phase containing cationic, anionic or nonionic surfactants, passing the crude emulsion through a high-pressure homogenizer and finally removing the solvent by evaporation at reduced pressure. In principle, according to the above patents, practically any polymer which is simultaneously insoluble in pure water and soluble in an organic solvent which is not miscible with water can be converted into an aqueous dispersion.

Pseudo-latexes are currently offered particularly as aqueous coating means or as medication vectors. During prolonged storage periods, however, a progressive loss of stability is noted, due, among other things, to the phenomenon of irreversible hydrolysis or flocculation. These pseudo-latexes sometimes contain high proportions of surfactants, which can render them unsuitable for certain purposes, especially pharmaceutical ones. In addition, for a given proportion of particles in liquid dispersion, it is necessary to transport large volumes of liquids, which is very costly on an industrial scale.

At present, desiccation of such pseudo-latexes for the purpose of obtaining therefrom a powder which can subsequently, at a desired time, be redispersed in an aqueous medium, implies prior addition to the liquid dispersion (pseudo-latex) of large proportions of surfactants or protective agents which remain behind in the resulting powder.

On the other hand, several processes for obtaining dried redispersible latex powders are known, but these are only applicable to a small number of water-insoluble polymers. U.S. Pat. No.4,462,839 describes a process for preparing powdered pseudo-latexes of cellulose acetophthalate, hydroxypropylmethylcellulose phthalates and polyvinyl acetophthalate. This technique is based on the addition of tribasic phosphates to the latex, followed by drying by atomization. The same authors (EP 0,111,103) describe a technique for obtaining a redispersible powdered pseudo-latex of cellulose acetophthalate, designed for coating purposes, involving the addition to the preformed pseudo-latex of an acetylated monoglyceride and then drying by atomization. In addition, U.S. Pat. No. 2,800,463 describes the conversion of a polyvinyl acetate latex into a powder which can be redispersed by adding a protective hydrocolloid (polyvinyl alcohol, gum arabic, gum, tragacanth, etc.), again followed by drying by atomization.

Thanks to the present invention, it is now possible to obtain, easily and with practically no limitation, microparticles of water-insoluble polymers in the form of easily redispersible powders, as well as pseudolatexes in the liquid dispersion state, without being faced with the disadvantages enumerated above. The invention is defined in particular in claims 1 and 9. The invention is based on the discovery that certain organic solvents, although miscible in all proportions with pure water, lead to the formation of a two-phase liquid-liquid system when they are added to concentrated aqueous solutions of a salt or even of a substance not subject to electrolytic dissociation.

Selection of the solute is just as critical as that of the solvent, and all combinations resulting in precipitation of the solute in solid form are, of course, unsuitable. The condition of complete miscibility between the solvent and pure water is not, on the other hand, essential, but contributes advantageously to proper execution of the process according to the present invention.

To obtain a redispersible pseudo-latex powder from a water-insoluble polymer, the first step, according to the invention, is to prepare a concentrated aqueous solution of a solute, to which a water-soluble macromolecular substance is added in sufficient quantity to produce a viscous solution or a gel.

It is possible to use a salt such as a mineral salt, such as magnesium, aluminum or sodium chloride, for example, or a metal sulfate, sulfite, nitrate, carbonate or phosphate as the solute. It is also possible to use a nonelectrolyte, such as a sugar-like glucose or sucrose, for example. The quantity of solute added will preferably be such that the aqueous solution is saturated or practically saturated, or more generally, sufficiently concentrated in solute that, once it is suitably mixed with the above-mentioned organic phase, it causes precipitation of the polymer microparticles.

As indicated, a water-soluble macromolecular substance is added to the said solution, designed to act as a protective hydrocolloid, at both the product preparation stage and the finished product stage, once the finished product has been redispersed in an aqueous medium. A water-soluble macromolecular polysaccharide such as gum arabic or gum tragacanth or a water-soluble polypeptide such as gelatin can be used as this substance. It is also possible to use a water-soluble polymer of synthetic origin, polyvinyl alcohol in particular. This list is not, however, exhaustive.

The water-soluble macromolecular substance is added to the concentrated aqueous solution in a quantity such that a gel or at least a viscous solution is finally obtained. The quantity added will depend on the nature of the said substance as well as the solute concentration.

Separately, a solution of the selected polymer is prepared in an organic solvent which is at least partially miscible with water, such as an alcohol, a polyalcohol or a ketone, for example. It is preferable to use an organic solvent which is miscible with water in all proportions, since this correspondingly facilities elimination thereof by repeatedly washing with water at the end of the process. The solvent should also be selected on the basis of its volatility and low toxicity, especially in view of the pharmaceutical application of the resulting product, for example, acetone, ethyl alcohol or isopropyl alcohol.

The above-mentioned concentrated aqueous phase, most generally in the form of a gel or a viscous solution, is then incorporated, under vigorous mechanical agitation, into the organic solution of the polymer, yielding, when addition has finished, an emulsion of the oil-in-water type. This operation is performed by means of the usual techniques at ambient temperature or even at low temperature, zero degrees C or even lower, depending on the nature of the products being treated. If desirable, the resulting emulsion can be subjected to a complementary homogenization operation, although this remains optional.

In accordance with the invention, pure water is then added to the resulting emulsion in sufficient quantity so that all of the organic solvent diffuses into the aqueous phase, thus causing the formation of microparticles of polymer suspended in the said aqueous phase. The water is added in the conventional way at the temperatures indicated above.

The resulting microparticles of polymer, generally present in spherical form, are first of all collected by sedimentation or centrifugation, and then, after elimination of the supernatant organic-aqueous phase, subjected to as many washings as necessary. The microparticles are washed by suspending them in water, with the addition, if necessary, of an organic solvent (for example, alcohol), which makes it possible to perform such an operation at low temperature. Any traces of excess solute and excess water-soluble macromolecular substance (protective hydrocolloid) are thereby eliminated.

A pseudo-latex in the liquid dispersion state can then easily be obtained at this stage of the operation by simply suspending the microparticles in water after the last washing stage.

The pseudo-latexes obtained in this manner are found to be, in the liquid dispersion state, extremely resistant to the addition of electrolytes, in contrast to pseudo-latexes prepared using methods known hitherto. This should facilitate the incorporation into the aqueous phase of medications or any other adjuvant. In addition, as a result of steric stabilization, rheological properties (low viscosity) and gelling resistance are greatly improved. The protective hydrocolloid, which is not solidly anchored to the surface of the pseudo-latex microparticles, is eliminated during the washing stage. This ensures that a product appropriate for coating applications and for the manufacture of films and membranes, such as those encountered especially in the pharmaceutical field, will be obtained. Irritating effects due to the presence of surfactant products in pseudo-latexes according to the prior art are also eliminated since no surfactant substance is incorporated during the process.

To produce the redispersible pseudo-latex powder, the microparticles of polymer are dried using any appropriate technique, once the washing operation is finished. One preferred drying technique is freezedrying; it also has the advantage of promoting redispersion of the powdered product which is produced. In addition, it is performed at a very low temperature, which is of capital importance when heat-sensitive polymers are used. In certain cases, of course, air drying or drying by atomization can be used.

The dried pseudo-latex powder rapidly redisperses in an aqueous medium, forming practically no clumps, under gentle agitation applied either manually or mechanically or with ultrasound.

By varying the agitation speed during the operation of mixing the aqueous phase (solute) and organic phase (polymer) and by using or not using the complementary homogenization stage or again by modifying the concentration of the polymer solution, it is possible to obtain particles with very different average sizes, ranging between 100 nm and 50 um.

Among the numerous advantages of the process described above, the following may be mentioned.

The process according to the invention does not at any time require an increase in temperature, unlike methods which utilize an organic solvent evaporation stage or a spray-drying stage. Indeed, it is even possible to perform the process at a low temperature ($-20°$ C.), thanks to the presence of electrolyte in the aqueous phase. Since the pseudo-latex is not coagulated by the addition of a certain proportion of organic solvent to the continuous phase, it is possible, if applicable, to use a mixture of water and organic solvent for washing in lieu of pure water. This capability of working at low temperature can be an important advantage when biopolymers are being manipulated, or when heat sensitive substances such as peptides or antibiotics are to be added.

The process according to the invention is applicable, in principle, to all water-insoluble polymers, provided the latter are soluble in an organic or mineral solvent and even to certain polymers which are soluble in water but insoluble in an aqueous solution that is concentrated in solute. In the latter case, however, it is best to cross-link the polymer that has thus been salted out so as to make it insoluble in pure water.

Certain water-insoluble polar polymers, such as cellulose, cellulose acetate or the polysulfones, do not dissolve easily except in solvents which are miscible with water. From this point of view, the proposed process facilitates or makes possible the production of pseudo-latexes from this type of polymer.

Since a number of medication substances are salted out in saline solutions, this makes it possible to envisage the incorporation of medications, in solution or in suspension, into the polymer particles, and thereby to obtain spherical filled microparticles by an unpublished method.

The examples below illustrate the invention in a more detailed manner without limiting it in any way.

EXAMPLE 1

Preparation of a Cellulose Acetate Redispersible Pseudolatex Powder (a) 911.2 g of magnesium chloride hexahydrate are dissolved in 588 g of water, and then 60 g of polyvinvl alcohol (molecular weight 100,000) are added with agitation. The resulting gel is allowed to stand for 24 hours.

(b) 100 g of cellulose acetate (AC 398-10, Eastman Kodak) are dissolved in 400 g of technical grade acetone.

(c) 693 g of the gel prepared in a) are slowly added (total time 20 minutes) and with agitation (motorized anchor stirrer, 350 rpm) to the organic solution obtained in b). 1000 ml of water are added to the resulting emulsion. The pseudo-latex which results is then placed in polycarbonate tubes and is centrifuged (seven minutes, 16,000 rpm). The sediment is collected, resuspended in water, placed back in the tubes and again centrifuged. This operation is repeated until the chloride reaction (addition of silver nitrate to the supernatant solution) becomes negative.

(d) The sediment is then resuspended in 30 ml of water, distributed into six one-liter flasks, cooled to −40° C. and freeze-dried.

The freeze-dried powder is greasy and can easily be redispersed in water with gentle agitation (particle size as measured with a Coulter Nano-Sizer: sample before drying: 1223 ±169 nm; sample redispersed in aqueous phase: 1157±169 nm).

EXAMPLE 2

Preparation of a Cellulose Acetate Redispersible Pseudolatex Powder 138.6 g of polyvinyl alcohol and 100 g of an acetone solution of cellulose acetate (same compositions as in the previous example) are mixed, and then the emulsion is homogenized (turbine type mixer) for three minutes. 200 ml of water are added, and then the resulting product is treated as in the previous example, step (d). The homogenization stage has made it possible to reduce the average particle size to 380 nm.

EXAMPLE 3

Preparation of a Cellulose Acetophthalate Redispersible Pseudo-latex Powder 120 g of a 20 wt. % solution of cellulose acetophthalate (Eastman Kodak, U.S.P. grade) are prepared, to which are slowly added 166.4 g of a polyvinyl alcohol gel prepared as in Example 1, with agitation, followed by 240 ml of water. Washing and freeze-drying are performed as for cellulose acetate and produce an easily redispersible product with an average particle size of about one micron.

We claim:

1. A process for preparing a powder of water-insoluable polymer which can be redispersed in a liquid phase, comprising the steps of:
    (a) preparing a concentrated aqueous solution of a solute to which is added a water-soluble macromolecular substance in a quantity sufficient to produce a viscous solution or a gel;
    (b) separately preparing a second solution of water-insoluable polymer, said polymer selected from the group consisting of cellulose and cellulose derivatives, ethylene/vinyl acetate copolymer, styrene/maleic anhydride copolymer, polymethacrylates, polysulfones, polyvinyl acetate phtalates, polylactic acids, polyglycolic acids and copolymers thereof, in an organic solvent, said solvent being a single organic compound which is at least partially miscible with water,
    (c) mixing, with agitation, the solution of (a) with the solution of (b) to create an emulsion;
    (d) adding water in sufficient quantity for all of the organic solvent to diffuse into the aqueous phase to cause the formation of microparticles of polymer in suspension in the aqueous phase;
    (e) removing the excess solute and water-soluble macro-molecular substance by repeated washing with water, and then collecting and drying the microparticles.

2. The process according to claim 1, wherein aqueous solution of solute is a saturated or practically saturated solution.

3. The process according to either claims 1 or 2, characterized by the fact that the water-soluble macromolecular substance is a polysaccharide or a water-soluble polypeptide of natural origin or a water-soluble synthetic polymer.

4. The process according to any of claims 1 through 4 wherein that the solute is an electrolyte or a nonelectrolyte.

5. The process according to any of claims 1 or 2 wherein the fact that the organic solvent for the polymer is miscible with water in any proportion.

6. The process according to claim 1 including a stage of homogenizing the emulsion obtained in step (c).

7. A process for preparing a dispersion in the liquid phase of a powdered water-insoluble polymer, comprising suspending the polymer powder obtained by means of the process according to claim 1 in water.

8. A process for preparing a water-insoluble polymer in the liquid dispersion state, comprising the steps of:
    (a) preparing a concentrated aqueous solution of a solute to which is added a water-soluble macromolecular substance in a quantity sufficient to produce a viscous solution or a gel;
    (b) separately preparing a solution of a water-insoluble polymer, said polymer selected from the group consisting of cellulose and cellulose derivatives, ethylene/vinyl acetate copolymer, styrene/maleic anhydride copolymer, polymethacrylates, polysulfones, polyvinyl acetate phtalates, polylactic acids, polyglycolic acids and copolymers thereof, in an organic solvent, said solvent consisting essentially of a single organic solvent which is at least partially miscible with water;
    (c) mixing, with agitation, the aqueous mixture above in step (a) above with the organic polymer solution obtained in step (b) to create an emulsion;
    (d) adding water in sufficient quantity for all of the organic solvent to diffuse into the aqueous phase of the resulting emulsion, to cause the formation of microparticles of polymer in suspension in the aqueous phase;
    (e) eliminating the excess solute and water-soluble macro-molecular substance by repeated washing with water and then maintaining the washed micro-particles in suspension in a suitable portion of water.

9. The process according to claim 3 wherein the water-soluble synthetic polymer is polyvinyl alcohol.

10. The process according to claim 4 in which the electrolyte is a mineral salt.

* * * * *

UNITED STATES PATENT AND TRADEMARK OFFICE
CERTIFICATE OF CORRECTION

PATENT NO. : 4,968,350

DATED : Nov. 6, 1990

INVENTOR(S) : BINDSCHAEDLER et al.

It is certified that error appears in the above-identified patent and that said Letters Patent is hereby corrected as shown below:

On the title page item [76]:

In the address of the inventor, change "Genthold" to --Genthod--.

Column 5, line 48, change "phtalates" to --phthalate--.

Column 6, line 38, change "phtalates" to --phthalate--.

UNITED STATES PATENT AND TRADEMARK OFFICE
CERTIFICATE OF CORRECTION

PATENT NO.   : 4,968,350

DATED        : Nov. 6, 1990

INVENTOR(S)  : Bindschaedler et al.

It is certified that error appears in the above-identified patent and that said Letters Patent is hereby corrected as shown below:

Column 5, line 36, change "insoluable" to --insoluble--; and
         line 44, change "insoluable" to --insoluble--.

Column 6, lines 13-14, change "through 4" to --or 2--;
         line 14, delete "that";
         line 17, delete "the fact that"; and
         line 41, change "above" to --obtained--.

Signed and Sealed this

Twenty-first Day of April, 1992

Attest:

HARRY F. MANBECK, JR.

*Attesting Officer*               *Commissioner of Patents and Trademarks*